US007812308B2

(12) United States Patent
Kobayashi

(10) Patent No.: US 7,812,308 B2
(45) Date of Patent: Oct. 12, 2010

(54) MASS SPECTROMETER

(75) Inventor: Masato Kobayashi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 213 days.

(21) Appl. No.: 12/067,128

(22) PCT Filed: Sep. 16, 2005

(86) PCT No.: PCT/JP2005/017191
§ 371 (c)(1),
(2), (4) Date: Mar. 17, 2008

(87) PCT Pub. No.: WO2007/032088
PCT Pub. Date: Mar. 22, 2007

(65) Prior Publication Data
US 2009/0236518 A1 Sep. 24, 2009

(51) Int. Cl.
H01J 49/00 (2006.01)
(52) U.S. Cl. .................. 250/288; 250/281; 250/282; 250/285; 250/432 R; 250/292
(58) Field of Classification Search .......... 250/281, 250/282, 285, 288, 423 R, 292
See application file for complete search history.

(56) References Cited
U.S. PATENT DOCUMENTS
5,668,370 A 9/1997 Yano et al.
6,646,257 B1 11/2003 Fischer et al.

FOREIGN PATENT DOCUMENTS
JP 2000-088808 A 3/2000
JP 2002-157971 A 5/2002
JP 2004-185886 A 7/2004
JP 2004-294453 A 10/2004
JP 2005-528746 A 9/2005
WO 03/102537 A2 12/2003

OTHER PUBLICATIONS

M. M. Siegel et al.: "Evaluation of a Dual Electrospray Ionization/Atmospheric Pressure Chemical Ionization Source at Low Fow Rates (~ 50 muL/min) for the Analysis of Both Highly and Weakly Polar Compounds" Journal of the American Society for Mass Spectrometry, Elsevier Science Inc, US, vol. 9, No. 11, Nov. 1, 2008, pp. 1196-1203, XP004142529, ISSN: 1044-0305.
R. King et al.: "Mechanistic investigation of ionization suppression in electrospray ionization" Journal of the American Society for Mass Spectrometry, Elsevier Science Inc, US, vol. 11, No. 11, Nov. 1, 2000, pp. 942-950, XP004224829, ISSN: 1044-0305.
Daniel D. Ebeling, et al., "Corona Discharge in Charge Reduction Electrospray Mass Spectrometry", Anal. Chem., 2000.11.1, vol. 72, No. 21, p. 5158-5161.

Primary Examiner—Jack I Berman
Assistant Examiner—Meenakshi S Sahu
(74) Attorney, Agent, or Firm—Sughrue Mion, PLLC

(57) ABSTRACT

In a liquid chromatograph mass spectrometer having an ionization interface capable of simultaneously performing ionization operations by ESI and APCI, a spray nozzle 22 for spraying a liquid sample given form a liquid chromatograph section as charged droplets, and a corona discharger 25 for ionizing mobile phase solvent molecules are placed in the same ionization chamber 21. The same voltages are applied to both the spray nozzle and the corona discharger from a single high-voltage power supply 41. The electrical power's value of the heater 27 of the heated dry gas supplier for drying the charged droplets generated in the spray nozzle 22 are set to be suitable for the ionization according to APCI. Consequently, the labor for the circuit design and the number of the parts are reduced. At the same time, the parameter setting items for the user are decreased, which leads to enhanced operability.

4 Claims, 2 Drawing Sheets (a) ESI (b) APCI

MASS SPECTROMETER

TECHNICAL FIELD

The present invention relates to a mass spectrometer, and in particular to an ionization interface for ionizing a liquid sample supplied from a liquid chromatograph or other devices and then introducing it to a mass spectrometer section.

BACKGROUND ART

FIG. 3 is a schematic configuration diagram illustrating one example of a conventionally-known general liquid chromatograph mass spectrometer (LC/MS). A sample liquid temporally separated and eluted from a column 11 of a liquid chromatograph section (LC section) 10 is introduced into an interface section (atmospheric pressure ionization interface) 20, and is then sprayed from a spray nozzle 22 into an ionization chamber 21 to be ionized. Fine droplets including ions generated go inside a tubule (desolvation tube) 23 placed ahead and are sent to a mass analysis section (MS section) 30. The desolvation tube 23 is warmed by a heater (which is not shown) and the evaporation of the solvent in the droplets progresses while the solvents pass thorough inside the desolvation tube 23 to further continue the generation of the target ion.

The MS section 30 is composed of three chambers; a first intermediate chamber 31, a second intermediate chamber 32, and an analysis chamber 33. The ionization chamber 21 and the first intermediate chamber 31 communicate with each other through the desolvation tube 23. The first intermediate chamber 31 and the second intermediate chamber 32 communicate with each other through a passage hole (orifice) 36 with a small diameter placed on the top of a conical skimmer 35. Inside the ionization chamber 21, an atmosphere is maintained at approximately atmospheric pressure. The first intermediate chamber 31 is exhausted to approximately 1 Torr by a rotary pump. The second intermediate chamber 32 and the analysis chamber 33 are respectively exhausted to approximately $10^{-3}$-$10^{-4}$ Torr and to approximately $10^{-5}$-$10^{-6}$ Torr by a turbo molecular pump. The analysis chamber 33 is maintained in a high-vacuum state by heightening the degree of vacuum in a stepwise manner from the ionization chamber 21 to the analysis chamber 33.

The ions that have passed through the desolvation tube 23 are converged into the orifice 36 by a first ion lens 34, and pass through the orifice 36 to be introduced into the second intermediate chamber 32. The ions are then converged and accelerated by a second ion lens 37 to be sent to the analysis chamber 33. Only the target ions having a particular mass number (mass/charge) pass through the space across the long axis of a quadrupole filter 38 placed in the analysis chamber 33 and reach an ion detector 39. In the ion detector 39, a current corresponding to the number of the ions reached is taken out as a detection signal.

In the aforementioned configuration, the interface section 20 ionizes various kinds of sample components included in a sample liquid by atomizing the sample liquid by heating, high-speed gas stream, high electric field, etc. As the ionization method, an electrospray ionization (ESI) method and atmospheric pressure chemical ionization (APCI) method have been most widely used.

FIG. 4(a) illustrates a configuration example of an ionization spray section according to an ESI method. In ESI, a DC (direct current) high voltage of approximately several kV is applied to the tip portion of the spray nozzle 22 to generate a strong non-uniform electric field. The sample liquid that has reached the tip of the spray nozzle 22 is charge-separated by this electric field, and is sprayed as micro-charged droplets into the ionization chamber 21 with the assistance of a nebulizer gas blown from a nebulizer tube (not shown) placed concentrically around the spray nozzle 22. In the ionization chamber 21, a heated dry gas is supplied from a dry gas supply port 24, which is placed around the desolvation tube 23, by a heated gas supplier which is not shown. The heated dry gas is sprayed in a mist flow and the evaporation of the solvent in droplets accordingly progresses to proceed the generation of gaseous ions.

FIG. 4(b) illustrates a configuration example of an ionization spray section according to an APCI method. In the APCI method, a needle-like discharging electrode 25 is placed in front of a spray nozzle 22. A sample liquid is sprayed into a heater 26, which is placed to encircle the tip of the spray nozzle 22, by using a nebulizer gas. Consequently the solvent and the sample molecules are vaporized. The sample molecules are made to chemically react by carrier gas ions (buffer ions) generated by a corona discharge from the discharging electrode 25. Accordingly, the ionization is carried out.

In general, an APCI is effective to ionize low-polarity through middle-polarity compounds, and ESI is effective to ionize middle-polarity through high-polarity compounds. In addition, in an ESI, since multivalent ions are generated in the process of ionizing protein or other substances, it is possible to measure compounds having several tens of thousands of molecular weights, which are beyond the upper limit of the apparatus' mass range. Therefore, both ionization methods are used according to the kind of sample to be analyzed, the analytical objective, etc. Conventionally, in a general LC/MS, an ESI spray section and an APCI spray section can be easily changed; the analyst properly changes the spray section according to the ionization method. Since such changing operation causes much trouble, however, this is one of the reasons to decrease the analytical efficiency.

Given this situation, in order to save such changing labors, some conventionally-proposed apparatuses have both ionization means in the same ionization chamber. For example, Patent Document 1 and Patent Document 2 describe an ionization interface using a common spray nozzle for ESI and APCI. With these interfaces, it is possible to perform an ionization according to ESI by applying a direct current high voltage to the tip of a spray nozzle, and concurrently, it is possible to perform an ionization according to APCI by a corona discharge by a discharging electrode placed on the tip of the spray nozzle.

[Patent Document 1] U.S. Pat. No. 6,646,257
[Patent Document 2] International Publication Pamphlet No. 03/102537

DISCLOSURE OF THE INVENTION

Problem to be Solved by the Invention

Conventionally, in an apparatus as previously described having a spray nozzle (electrostatic spray) for generating charged droplets and a discharging electrode (corona discharger) for performing a corona discharge, an appropriate high voltage for each of the electrostatic spray and the corona discharger is independently supplied. Alternatively, a high voltage is alternately supplied to the electrostatic spray and the corona discharger from a single power supply. In the case where independent voltages are supplied to each, however, at least a two-channel voltage control circuit is required. In the case where a high voltage is alternately supplied, a switching circuit is required. Accordingly, there have been problems such as; the labor and cost for a circuit design increase, and the operation is complicated because parameter options (the value of a voltage to be applied to both the electrostatic spray and the corona discharger, the timing for switching the voltage supply, or other options) for the user increases.

Since any ionization method according to ESI or APCI requires droplets in a mist flow to be dried, conventional LC/MSs having two types of ionization means accelerate the evaporation of a solvent by blowing a heated gas as in the case with the aforementioned normal ESI. In this method, however, the quantity of heat to be supplied to droplets per unit time is relatively small. Hence, although this method is suitable for the ionization according to ESI, a sufficient ionization efficiency cannot always be obtained in APCI. For this reason, the ionization efficiency in APCI is enhanced by placing an extra heater in front of a spray nozzle or with other methods. However, this causes a problem of a device configuration's complication, which leads to a higher production cost.

The present invention is developed in view of the aforementioned problems and the main objective thereof is to provide an LC/MS that has an ionization interface with both an electrostatic spray and a corona discharger, is user-friendly, and can be produced at low cost.

Means for Solving the Problems

To solve the aforementioned problems, the present invention provides a mass spectrometer having an ionization interface for making a liquid sample ionized and introduced into a mass spectrometer section, including:

a) an electrostatic spray for spraying a liquid sample as charged droplets;

b) a corona discharger, placed in front of the electrostatic spray, for generating a corona discharge for ionizing a mobile phase solvent molecule; and c) a voltage supplier for supplying a voltage to the electrostatic spray and the corona discharger, wherein:

the voltage supplier supplies voltages of a same value to the electrostatic spray and the corona discharger from a single high-voltage power supply.

In the mass spectrometer according to the present invention, it is preferable that the voltage supplier may include a bifurcator for bifurcating a feeder cable connected to the high-voltage power supply into two directions in a housing, one bifurcated cable may be connected to the corona discharger, the other bifurcated cable may be connected to a feeder port placed on a surface of the housing, and a feeder cable connected to the electrostatic spray may be detachably connected to the feeder port.

Effects of the Invention

Since the LC/MS according to the present invention as described earlier simultaneously applies the same voltage to both the electrostatic spray and the corona discharger, the labor for a control circuit design and the number of parts are reduced, which leads to a lower production cost. Another advantage is that parameter setting items for the user are reduced, which simplifies the operation. Such mass spectrometer according to the present invention simultaneously performs ionizations according to ESI and APCI; hence, it can be preferably used for a high-throughput analysis intended for diverse samples.

In the case where the mass spectrometer includes the bifurcator as previously described, the voltage supplier can be configured by connecting a feeder cable leading out of the bifurcator to a high-voltage power supply and simultaneously connecting a feeder cable leading out of the electrostatic spray to a feeder port placed in the bifurcator. This brings about the advantage that an existing ESI probe can be used without modification.

EXPLANATION OF NUMERALS

10 . . . LC Section
11 . . . Column
20 . . . Interface Section
21 . . . Ionization Chamber
22 . . . Spray Nozzle
22a . . . Metal Tube
23 . . . Desolvation Tube
24 . . . Dry Gas Supply Port
25 . . . Discharging Electrode
26 . . . Heater
27 . . . Block Heater
30 . . . MS Section
31 . . . First Intermediate Chamber
32 . . . Second Intermediate Chamber
33 . . . Analysis Chamber
34 . . . First Ion Lens
35 . . . Skimmer
36 . . . Orifice
37 . . . Second Ion Lens
38 . . . Quadrupole Filter
39 . . . Ion Detector
40 . . . Controller
41 . . . High-Voltage Power Supply
42 . . . Power Supply
43 . . . Junction Box
44 . . . First Cable
45 . . . Second Cable
46 . . . Third Cable
46a . . . Power Feeding Port
47 . . . Feeder Cable

BEST MODE FOR CARRYING OUT THE INVENTION

Figure 1:
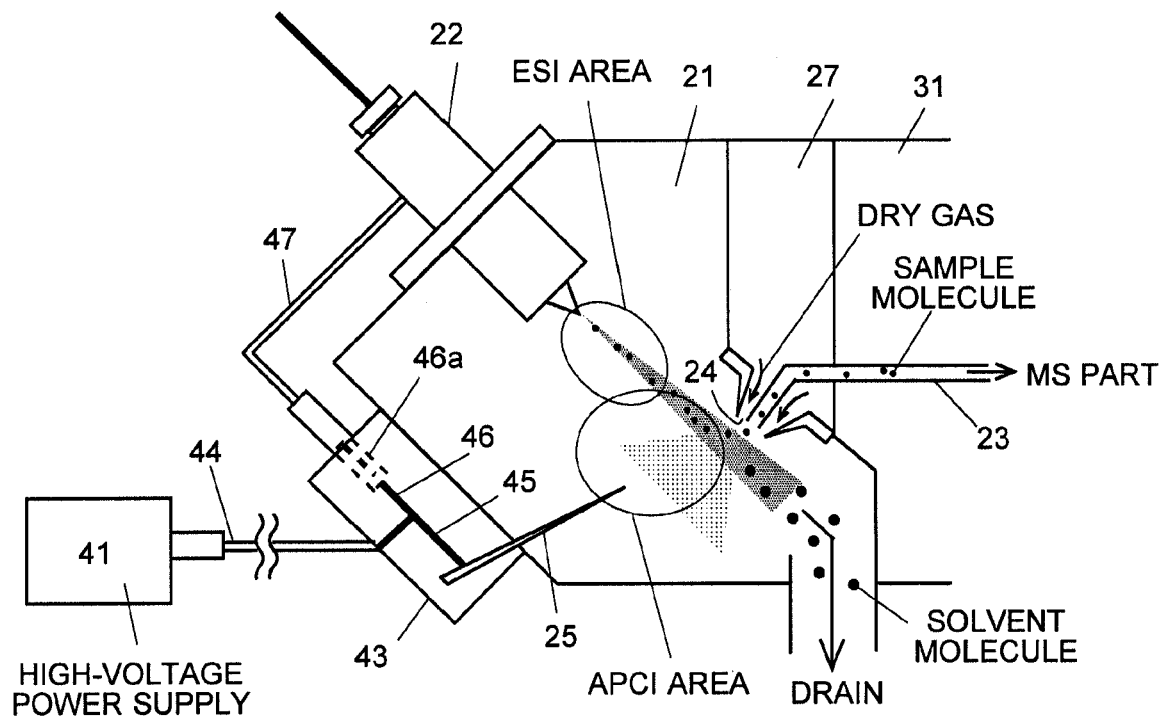
FIG. 1 is a schematic configuration diagram of an atmospheric pressure ionization interface section of the atmospheric pressure ionization mass spectrometer according to an embodiment of the present invention.
Figure 2:
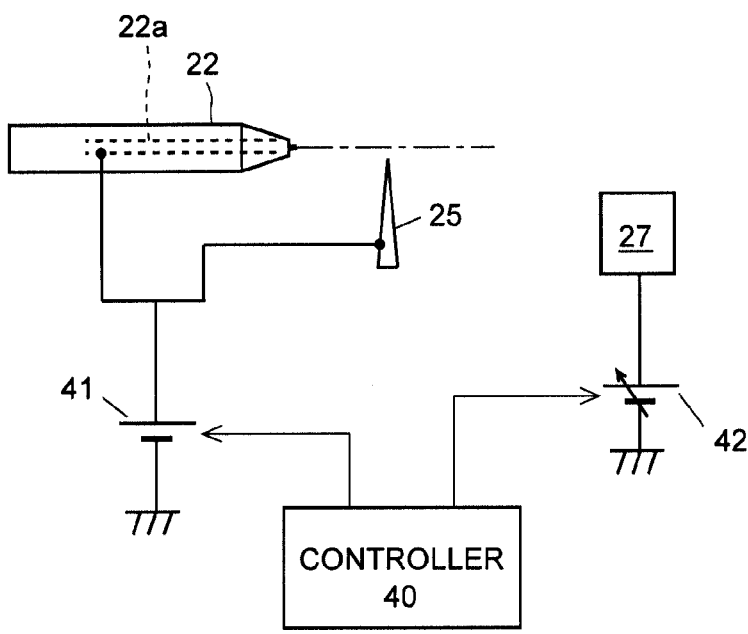
FIG. 2 is an electric schematic configuration diagram of the main portion of the atmospheric pressure ionization mass spectrometer according to the present embodiment.

Hereinafter, one embodiment of the atmospheric pressure ionization mass spectrometer according to the present invention will be explained with reference to the figures. FIG. 1 is a schematic configuration diagram of an ionization interface section of the atmospheric pressure ionization mass spectrometer according to the present embodiment. FIG. 2 is an electric schematic configuration diagram of the main portion of the mass spectrometer. The explanation for the basic configuration other than those aforementioned is omitted because it is similar to that of a conventional general MS which was explained with respect to FIG. 3.

As illustrated in FIG. 1, a spray nozzle 22 as an electrostatic spray and a needle-like discharging electrode 25 as a corona discharger are placed in an ionization interface section. These are placed in the position so that the optimum application voltage to both the electrostatic spray and the discharging electrode becomes identical. At the boundary of the ionization chamber 21 and the first intermediate chamber 31, a block heater 27 for heating a desolvation tube 23 and a dry gas supplied to the ionization chamber 21 are placed.

This ionization interface section can perform both ionization modes according to ESI and APCI. That is, as illustrated in FIG. 2, a high-voltage power supply 41 for supplying a high voltage of several kV or more is connected, by a feeder line having a bifurcation portion, to the discharging electrode 25 and to a metal tube 22a placed inside the spray nozzle 22. The on/off operation of the high-voltage power supply 41 is controlled by a controller 40 for handling the MS section's general actions. A voltage-variable power supply 42 is connected to the block heater. The on/off operation and the output voltage of the power supply 42 are also controlled by the controller 40.

In the LC/MS according to the present embodiment, as illustrated in FIG. 1, a junction box 43 is placed among the high-voltage power supply 41, the spray nozzle 22, and the discharging electrode 25. In the junction box 43, the high voltage's destination is bifurcated. The first cable 44 which is detachably connected to the high-voltage power supply 41 leads out from the junction box 43, and, inside the junction box 43, the first cable 44 is bifurcated into the second cable 45 and the third cable 46. The second cable 45 is connected to the discharging electrode 25, and the third cable 46 is connected to a power feeding port 46a placed inside the junction box. The third cable 46 is detachably connected, via the power feeding port 46a, to a feeder cable 47 placed on the spray nozzle 22. Since the high voltage's destination is bifurcated by placing such a junction box 43, an existing ESI probe can be used without modification as a spray nozzle 22 of the present embodiment by connecting the ESI probe to the junction box 43.

The operation of the LC/MS according to the present embodiment when performing an analysis is now explained. A sample liquid separated in an LC section is introduced into the spray nozzle 22 from a sample tube connected to the rear of the spray nozzle 22. In this process, a high voltage V1 generated in the high-voltage power supply 41 is applied to the metal tube 22a in the spray nozzle 22 and to the discharging electrode 25.

The metal tube 22a surrounds a capillary tube which a sample liquid flows through. Therefore, the liquid sample which has reached the end portion of the capillary tube by the high voltage applied to the metal tube 22a becomes strongly-charged, and is sprayed as charged droplets with the assistance of a nebulizer gas sprayed from a nebulizer tube (not shown) which is an external cylinder of the capillary tube. A heated dry gas sprayed from a dry gas supply port 24 is misted to the mist flow, and the solvent in the droplets rapidly evaporates, which reduces the droplets' size. Along with this, gaseous ions are generated by Coulomb repulsion.

On the other hand, buffer ions are generated around the discharging electrode 25 by a corona discharge by the application of the aforementioned high voltage V1. The sample molecules in the mist flow are ionized by reacting with the buffer ions. In order to attain a high ionization efficiency in the APCI method, sample droplets are required to be sufficiently dried. However, in the interface according to the present embodiment, if the electrical power of the block heater is increased more than in conventional units, the high ionization efficiency can be attained without placing an extra heater.

The ions generated as just described are drawn into the first intermediate chamber 31 via the desolvation tube 23 by the pressure difference between the ionization chamber 21 and the first intermediate chamber 31. Micro droplets that have not been completely evaporated and remained in the ionization chamber 21 are also drawn into the desolvation tube 23. They are then heated in the tube by the block heater 27 so that the solvent is evaporated, which accelerates the ionization. The ions that have reached the first intermediate chamber 31 are converged by the first ion lens 34, and are sent to the second intermediate chamber and the analysis chamber in the subsequent stages.

As just described, in the ion source according to the LC/MS of the present invention, an ionization by the ESI method and an ionization by the APCI method are simultaneously performed by the electrostatic spray and the corona discharger. Hence, both a component suitable for ESI and a component suitable for APCI can be efficiently ionized in a single analysis. In addition, in the LC/MS according to the present embodiment, as described earlier, the voltages having the same value are applied from a single high-voltage power supply to the electrostatic spray and the corona discharger. Hence, the labor for designing the control circuit is reduced and the number of parts can be decreased. Furthermore, the labor for setting parameters by the user is reduced, which leads to a higher operability.

Figure 3:
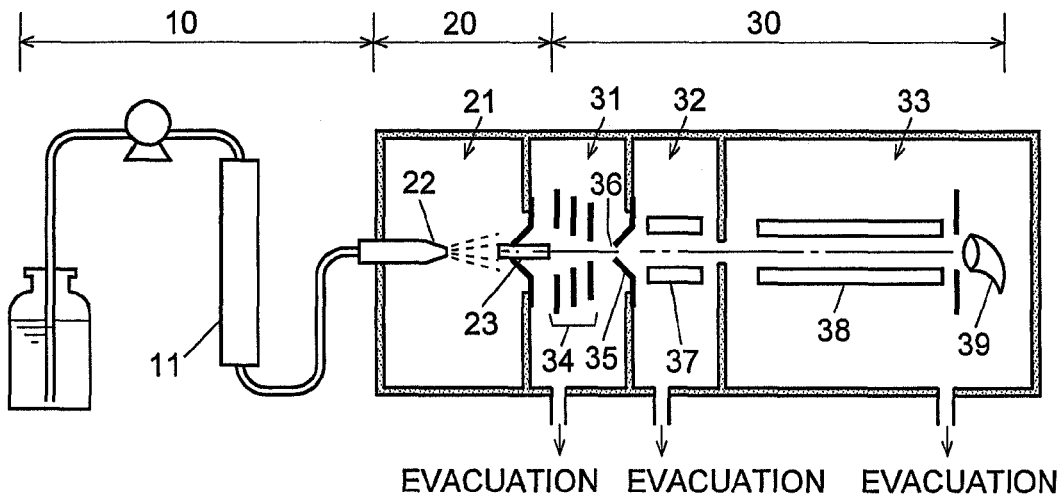
FIG. 3 is a schematic configuration diagram illustrating an example of a conventionally-known general LC/MS.
Figure 4:
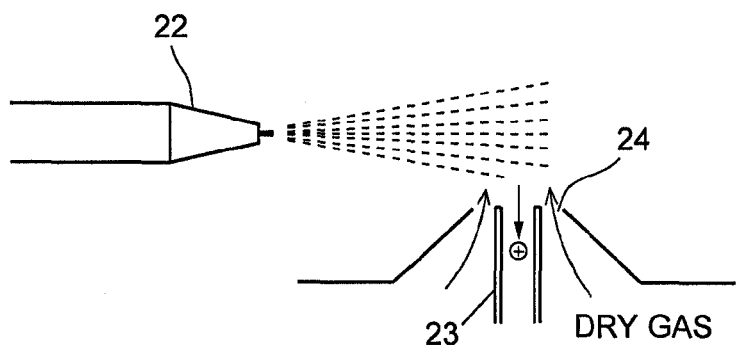
FIG. 4 is a schematic view illustrating a configuration example of various types of conventional ionization methods.
Figure 4:
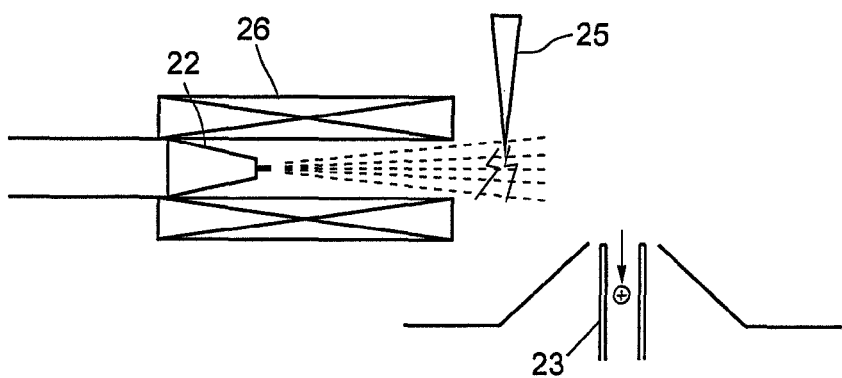

It should be noted that the aforementioned embodiment is an example; changes or modifications can be properly performed within the scope of the present invention. For example, the MS section according to the mass spectrometer of the present invention may include any type of mass separator such as a time-of-flight type or other type, other than a quadrupole filter as illustrated in FIG. 3. It is also possible to bifurcate the feeder line from the high-voltage power supply and make it directly connect to the electrostatic spray and the corona discharger, without a junction box as previously described.

The invention claimed is:

1. A mass spectrometer having an ionization interface for making a liquid sample ionized and introduced into a mass spectrometer section, comprising:
   a) an electrostatic spray for spraying a liquid sample as charged droplets;
   b) a corona discharger, placed in front of the electrostatic spray, for generating a corona discharge for ionizing a mobile phase solvent molecule; and
   c) a voltage supplier for supplying a voltage to the electrostatic spray and the corona discharger, wherein:
   the voltage supplier supplies voltages of a same value simultaneously to the electrostatic spray and to the corona discharger from a single high-voltage power supply.

2. The mass spectrometer according to claim 1, wherein the voltage supplier comprises a bifurcator for bifurcating a feeder cable connected to the high-voltage power supply into two directions in a housing, one bifurcated cable is connected to the corona discharger, the other bifurcated cable is connected to a feeder port placed on a surface of the housing, and a feeder cable placed in the electrostatic spray is detachably connected to the feeder port.

3. The mass spectrometer according to claim 1, wherein the electrostatic spray and the corona discharger are placed in a position where optimum application voltages to the electrostatic spray and to the corona discharger are identical.

4. The mass spectrometer according to claim 3, wherein the voltage supplier comprises a bifurcator for bifurcating a feeder cable connected to the high-voltage power supply into two directions in a housing, one bifurcated cable is connected to the corona discharger, the other bifurcated cable is connected to a feeder port placed on a surface of the housing, and a feeder cable placed in the electrostatic spray is detachably connected to the feeder port.

* * * * *